United States Patent
Rogers

Patent Number: 5,431,678
Date of Patent: Jul. 11, 1995

[54] PROTECTIVE SURGICAL SEWING NEEDLE

[76] Inventor: William D. Rogers, 363 Hill St., Southampton, N.Y. 11968

[21] Appl. No.: 318,965

[22] Filed: Oct. 6, 1994

[51] Int. Cl.$^6$ ............................................. A61B 17/04
[52] U.S. Cl. ................................. 606/223; 606/222; 606/224; 606/144
[58] Field of Search ............................ 606/222–228, 606/144–145, 139

[56] References Cited

U.S. PATENT DOCUMENTS

| | | | |
|---|---|---|---|
| 3,470,875 | 10/1969 | Johnson | 606/145 |
| 3,946,740 | 3/1976 | Bassett | 606/145 |
| 4,050,100 | 9/1977 | Barry | 623/15 |
| 4,382,444 | 5/1983 | Malmin | 623/15 |
| 4,557,265 | 12/1985 | Anderson | 606/144 |
| 5,181,919 | 6/1993 | Bergman et al. | 606/139 |
| 5,219,358 | 6/1993 | Bendel et al. | 606/139 |

*Primary Examiner*—Gary Jackson
*Attorney, Agent, or Firm*—Parkhurst, Wendel & Rossi

[57] ABSTRACT

A surgical sewing needle, including a generally arcuate needle body having a first end for receiving suture material and a second end which forms a sharp point, the needle body being flexible between closed and open positions, the first end protecting the second end in the closed position to prevent the sharp point from unintentional punctures, the needle body being biased such that the first and second ends are separated from each other in the open position to facilitate suturing.

3 Claims, 1 Drawing Sheet

PROTECTIVE SURGICAL SEWING NEEDLE

BACKGROUND OF THE INVENTION

1. Field of the Invention

The present invention is directed to a surgical sewing needle for suturing. Particularly, the present invention relates to a sewing needle which is rendered incapable of puncturing or otherwise needle-sticking anything, unless clamped by a surgical tool in an open position for suturing.

2. Related Art

FIG. 1 shows a typical prior art surgical needle 1, having first end 2 for receiving suturing material 4, and pointed end 3. That structure has a particular disadvantage in that the pointed end 3 remains exposed before and after suturing, and increases the chances of an accidental puncture-type injury and passage of containments.

U.S. Pat. No. 5,219,358 discloses a surgical needle that is made of a shape memory alloy. The needle has a low temperature state in which it is elongated such that it may easily pass through a tube used during endoscopic surgery. The needle also has a high temperature state, wherein it has a curved shape for suturing.

U.S. Pat. No. 5,181,919 discloses an elongated suturing device which is used in endoscopic surgery. The device includes an integral member having two prongs which terminate in arcuate-shaped suture carrying and grasping mechanisms. The mechanisms are manipulated via sliding movement of the prongs.

U.S. Pat. No. 4,557,265 discloses a suturing instrument that utilizes a needle disposed at one end of a tube. The needle is rotated via driving of a flywheel to sew tissue together.

U.S. Pat. No. 4,345,601 discloses a suturing needle having an outer housing and a needle extending from one end thereof. The needle is forced via movement of appendage 12 such that it is driven through tissue. Apparently, the needle is then withdrawn along the path in the tissue so as to retract into its housing.

U.S. Pat. No. 3,946,740 discloses a suturing device that is somewhat similar to the device shown in the '601 patent in that the needle passes through a housing. The needle then passes into tissue, and is gripped by an opposite arm such that it is pulled through the tissue.

U.S. Pat. No. 3,470,875 discloses forceps that use a pair of bullet-like needles having suturing material attached thereto. The needles are placed within a jaw portion, and upon clamping of the forceps about tissue, the needles pass through the tissue and into an opposing jaw.

Each of the state of the art suturing devices described above has a specialized function, is relatively complex, is costly to manufacture, and fails to provide adequate needle-stick protection. Accordingly, objectives of the present invention include provision of a simple and cost-effective surgical sewing needle which is adapted to prevent needle-stick injuries when not in use.

SUMMARY OF THE INVENTION

The invention provides a surgical sewing needle which has a generally arcuate needle body having a first end for receiving a suture material and a second end which forms a sharp point. The needle body is adapted to be flexible between open and closed positions such that in the closed position, the second end protects the sharp point and prevents unwanted punctures or needle-stick injuries. The closed position is a normal, unbiased state of the needle.

Further, the present surgical sewing needle is adapted to open to facilitate suturing, whereby the needle is elongated and the first and second ends are separated from each other. This may be accomplished by providing a spring-loop portion along the needle body which, upon compression, forces opening of the needle. Additionally, the present surgical sewing needle maintains its open position only upon continued biasing or compression of the spring-loop portion. Accordingly, when a suturing tool such as surgical forceps is removed from the spring-loop portion, the needle is no longer externally biased and returns to the closed position.

DETAILED DESCRIPTION OF THE PREFERRED EMBODIMENT

Figure 1:
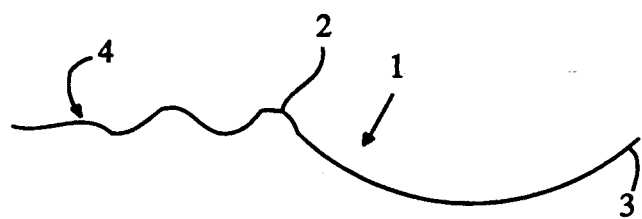
FIG. 1 is a side view of a typical prior art surgical needle.
Figure 2:
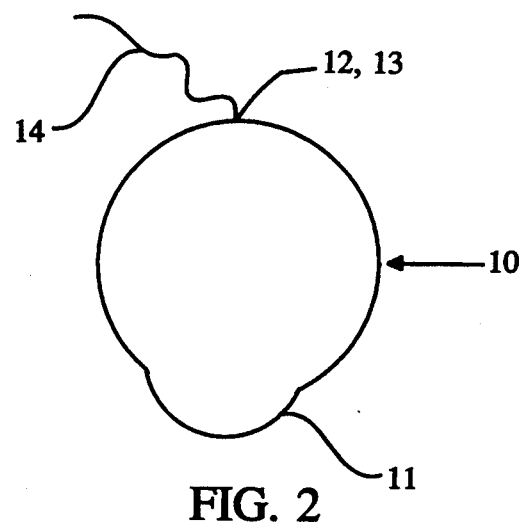
FIG. 2 is a side view of the present surgical needle, shown in its closed position.
Figure 3:
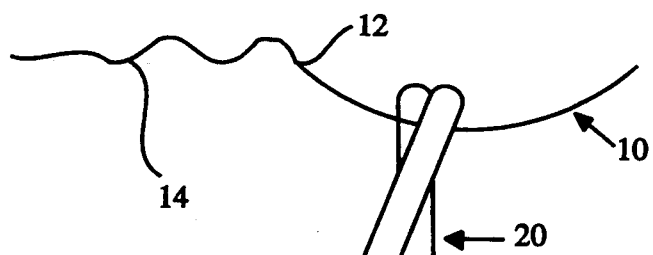
FIG. 3 is a side view of the present surgical needle in its open position and having forceps clamped thereon.
Figure 4:
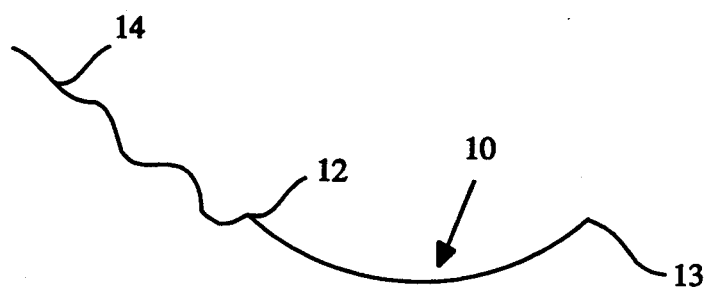
FIG. 4 is similar to FIG. 3, with the forceps removed.

FIGS. 2–4 of the present drawings show an embodiment of the present invention, including needle 10 having first and second ends 12 and 13, respectively, and spring-loop portion 11 formed along the length of needle body 10. First end 12 is adapted to receive suturing material 14, as well known in the art. Further, second end 13 forms a sharp point.

As shown in FIG. 2, the normal, unbiased state of the needle is such that the first and second ends 12 and 13 abut each other, thereby shielding the sharp point of second end 13. This closed position approximates a closed-loop structure to prevent needle-stick injuries.

In contrast, FIGS. 3 and 4 show open positions of the present surgical needle, whereby forceps 20 clamp onto spring-loop portion 11, thereby compressing spring-loop portion 11. Accordingly, the needle body 10 is forced into an open position to enable suturing.

Prior to suturing, the forceps 20 are clamped onto the needle 10, as shown in FIG. 3. Then, the second end 13 is passed through tissue of the patient until it is exposed through the tissue. The forceps are then released from needle 10, whereby the needle 10 returns to its closed position but allows passage of spring-loop portion 11 through the tissue. At that position, the needle 10 is then again clamped by forceps 20 at the spring-loop portion 11, thereby re-opening the needle 10. The suture is then finished by completely passing the needle 10 through the tissue.

While a particular embodiment of the invention has been shown and described, it will be understood that the invention is not limited thereto since many modifications may be made and will become apparent to those skilled in the art, without departing from the scope and spirit of the claims which follow. For example, in the closed position shown in FIG. 2, the needle may be adapted such that the first end overlaps or is spaced slightly apart from the second end 13.

What is claimed is:

1. A surgical sewing needle, comprising:
   a generally arcuate needle body having a first end for receiving suture material and a second end which forms a sharp point, said needle body being flexible between closed and open positions, said first end being adjacent said second end in said closed position to prevent said sharp point from unintentional punctures, said needle body being biased such that said first and second ends are separated from each other in said open position to facilitate suturing.

2. The needle of claim 1, further comprising a spring-loop portion along said needle body, whereby biasing of said spring-loop portion via compression thereof opens said needle body to facilitate suturing.

3. The needle of claim 1, wherein said needle body forms a closed-loop in said closed position, said first and second ends abutting each other.

* * * * *